United States Patent [19]

Tai et al.

[11] Patent Number: 4,687,475
[45] Date of Patent: Aug. 18, 1987

[54] METHOD FOR SEQUENTIAL INTRAVENOUS INFUSION OF MULTIPLE FLUIDS

[75] Inventors: Henry T. Tai, Pacific Palisades; Eric W. Brown, Redondo Beach, both of Calif.

[73] Assignee: I-Flow Corporation, Torrance, Calif.

[21] Appl. No.: 849,106

[22] Filed: Apr. 7, 1986

Related U.S. Application Data

[63] Continuation of Ser. No. 619,846, Jun. 12, 1984, abandoned.

[51] Int. Cl.$^4$ .............................................. A61M 5/14
[52] U.S. Cl. ...................................... 604/248; 604/81
[58] Field of Search .................................... 604/51-53, 604/80, 81, 152, 246, 248, 250, 410

[56] References Cited

U.S. PATENT DOCUMENTS

| | | |
|---|---|---|
| 3,057,350 | 10/1962 | Cowley . |
| 3,957,082 | 5/1976 | Fuson et al. ............... 604/80 |
| 4,094,318 | 6/1978 | Burke et al. . |
| 4,191,183 | 3/1980 | Mendelson . |
| 4,196,730 | 3/1980 | Wilson . |
| 4,219,022 | 8/1980 | Genese . |
| 4,256,103 | 3/1981 | Mylrea . |
| 4,257,416 | 3/1981 | Prager . |
| 4,258,712 | 3/1981 | Harms et al. . |
| 4,265,240 | 5/1981 | Jenkins . |
| 4,316,460 | 2/1982 | Genese et al. . |
| 4,324,238 | 4/1982 | Genese et al. . |
| 4,333,454 | 6/1982 | Hargest, III . |
| 4,391,598 | 7/1983 | Thompson . |
| 4,430,074 | 2/1984 | Mooring . |
| 4,450,079 | 5/1984 | Farr ................................ 604/152 |
| 4,512,764 | 4/1985 | Wunsch .............................. 604/80 |
| 4,563,175 | 1/1985 | LaFond ............................. 604/155 |

OTHER PUBLICATIONS

*Hickman* ® *and Broviac* ® *Vascular Access Catheters Instructions for Use* Evermed, Inc. Revised 1985.
Hutchinson, Margaret M., "Administration of Fat Emulsions", *American Journal of Nursing*, Feb. 1982.
Gray et al., "Multiple Use of TPN Catheter is Not Heresy: Retrospective Review and Initial Report of Prospective Study", *Nutritional Support Services*, vol. 2, No. 9, pp. 18-21, Sep. 1982.

*Primary Examiner*—C. Fred Rosenbaum
*Assistant Examiner*—Sherri E. Vinyard
*Attorney, Agent, or Firm*—Robert M. Asher

[57] ABSTRACT

A method of sequential intravenous infusion of a plurality of fluid solutions is disclosed in which a spacer solution is administered alternately with the fluid solutions to prevent the fluid solutions from substantially mixing with one another.

1 Claim, 9 Drawing Figures

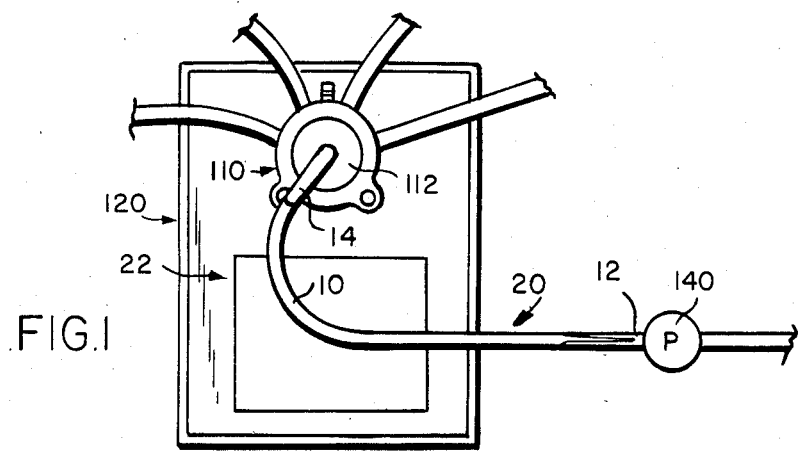
FIG.1
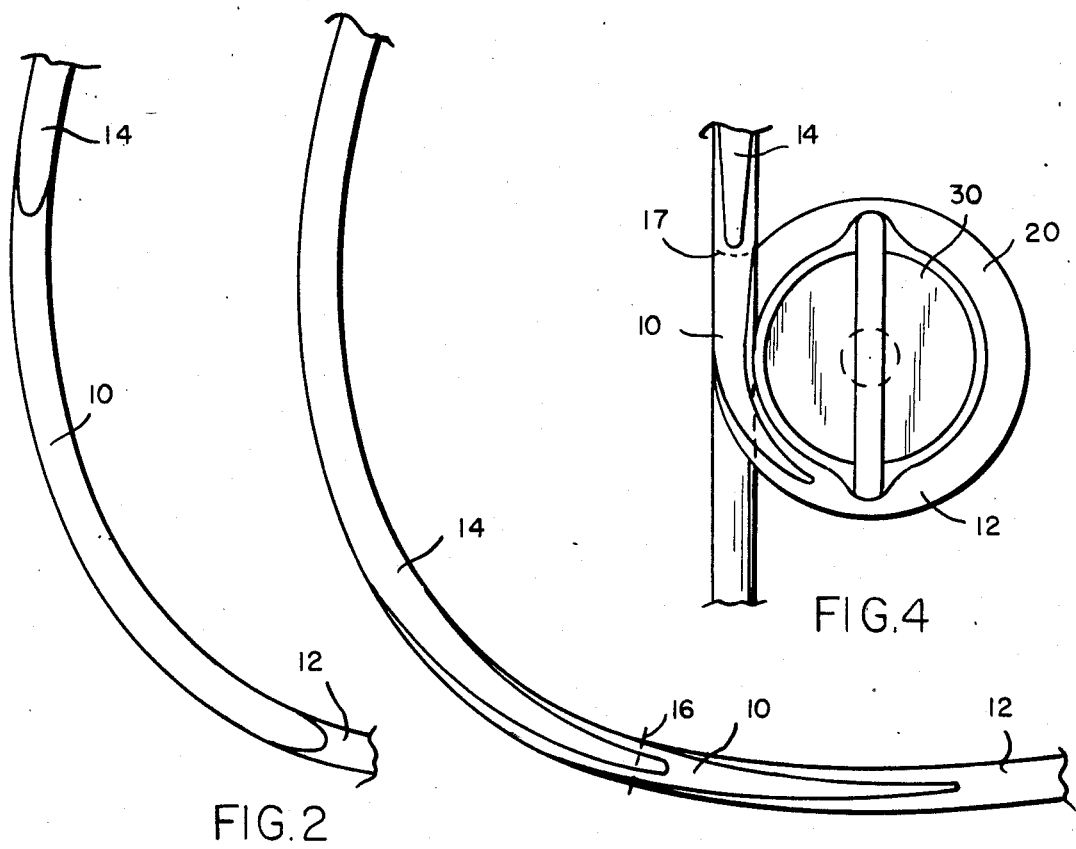
FIG.2
FIG.3
FIG.4
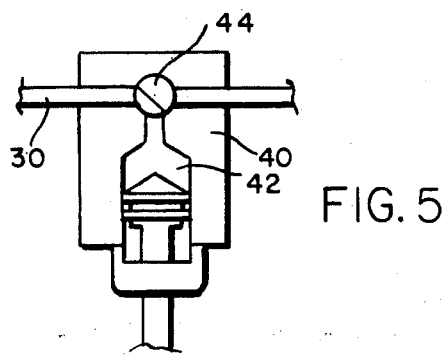
FIG.5

METHOD FOR SEQUENTIAL INTRAVENOUS INFUSION OF MULTIPLE FLUIDS

This is a file wrapper continuation of co-pending application Ser. No. 619,846, filed on June 12, 1984, now abandoned.

BACKGROUND OF THE INVENTION

This invention relates to the intravenous admininstration of multiple fluids.

There are many medical applications for which an intravenous infusion for a multiplicity of fluid solutions can be beneficial. One such application is chemotherapy infusions used in cancer treatment. This was recognized in the recent 13th Annual Cancer Course, given Mar. 1-3, 1984, by the Harvard Medical School and New England Deaconess Hospital. In the syllabus article entitled "Multi-Drug Infusion Chemotherapy: the Delivery of Two or More Drugs Simultaneously", Dr. Jacob J. Lokich described techniques for mixing drug solutions to form a combination which can be delivered to a patient by continuous intravenous infusion. The use of combination multi-drug chemotherapy has been developing in medicine since the 1960's. It has been used for such diseases as acute leukemia, Hodgkins disease, lung cancer, breast cancer and ovarian cancer. Unfortunately, there are only a limited number of drug combinations which have been found to be compatible and stable and which can produce a synergistic effect when administered.

There are many drugs which may not be used simultaneously because of reactions between the drugs which make infusion impracticable or undesirable. Some drugs react and thereby neutralize one another. Other drugs react to form precipitates which may clog the catheter tubing or even worse cause an embolism in the patient. Thus, according to present multi-drug combination treatments, physicians are limited in their choice of drug solutions.

SUMMARY OF THE INVENTION

This invention is directed to a method for sequential intravenous administration of fluid solutions. The method provides for administering a first fluid solution through a catheter tube followed by the contiguous administration of a predetermined amount of spacer solution. The spacer solution is then contiguously followed by a second fluid solution. Apparatus is provided for electronically changing the solution being provided from one to another. The amount of spacer solution which would be used between fluid solutions would be prescribed by the physician and should be large enough to prevent the first and second fluid solutions from substantially mixing.

The method of the present invention enormously increases the number of variations available to physicians for treating cancer and other diseases with multiple drug infusions. Since the intravenous spacer solution prevents the drug solutions from substantially mixing with one another before entering the body, drug solutions which were formerly incompatible because of deleterious reactions may now be tried as potentially beneficial treatments. Once a drug solution is infused into the patient the blood stream carries the drug away so quickly that it is usually safe to follow the drug solution with another solution after the spacer. By sequentially alternating between drug solutions and spacer solutions many new multiple drug treatments may be developed.

Other objects and advantages of the invention will become apparent during the following description of the presently preferred embodiments of the invention taken in conjunction with the drawings.

BRIEF DESCRIPTION OF THE DRAWINGS

FIG. 1 is an elevational view of an apparatus for performing the method of the present invention.

FIG. 2 is a sectional view of the catheter tube of FIG. 1 demonstrating the method of the present invention.

FIG. 3 is a cross-sectional view of the catheter tube of FIG. 1 after the spacer solution has been pumped through a length of catheter tubing.

FIG. 4 is an elevational view of a peristaltic pump for use in the method of the present invention.

FIG. 5 is an elevational view of a syringe-type cartridge pump for use in the method of the present invention.

DETAILED DESCRIPTION OF THE PREFERRED EMBODIMENTS

Figure 6:
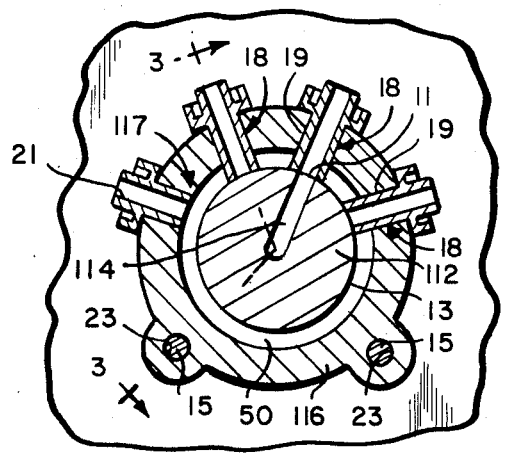
FIG. 6 is a cross-sectional view of a valve of the present invention.

Turning now to the drawings, FIG. 1 illustrates an apparatus for performing the method of the present invention. The apparatus is described in the inventors' copending application U.S. Ser. No. 619,847 entitled "Apparatus and Method for Administering Multiple Fluid Infusions", sharing the same filing date and assignee as the present invention. The inventors' copending application is hereby incorporated by reference herein. Their apparatus enables one to switch between different fluid solutions being intravenously administered through a catheter tube without allowing any air bubbles to enter into the line. A valve 110 receives inputs from a plurality of fluid solution sources and has a primary input for a spacer solution 10 source. The valve 110 switches between sources to alternately provide one of the fluid solutions and the spacer solution 10.

The valve 110 is mounted on control apparatus 120. The valve 110 is shown receiving four inputs from intravenous fluid solution sources. The valve 110 includes rotary core member 112. The rotary core member 112 has an output passageway 114 which is connected to a catheter tube 20 for delivering fluid to a patient. A pump 140 is coupled to the catheter tube for delivering the fluid at a predetermined speed. The pump 140 which is used with the present invention may be any conventional type of infusion pump. The presently preferred embodiment uses a peristaltic pump 30 which is especially well-suited for long duration infusions. The use of a syringe-type cartridge pump 40 is allowable for situations where a higher pressure is required and where larger fluid volumes may be infused into the patient.

Control apparatus 120 has a control panel 22 by which an operator can program the control apparatus 120 to infuse predetermined amounts of each fluid solution into the patient through the catheter tube 20. An operator would indicate to the apparatus 120 the quantity of each fluid to be pumped per unit time through the catheter tube. The apparatus 120 then computes the required pump speed and displays this information to the operator. The operator sets the pump 140 at this speed. The programmed apparatus automatically switches the valve 110 between fluid solutions to administer the prescribed regimen.

One of the inputs into the valve 110 is a neutral solution which is used as an isolator between drug solutions thereby preventing any substantial premixing of the solutions in the catheter tube 20. The control apparatus 120 will always alternate between the neutral solution and one of the drug solutions. This is the method of the present invention described below after the description of the apparatus.

It is highly important that the infused fluid solutions are not contaminated. Therefore, it is important that the valve 110 be sterile. The presently preferred embodiment employs a disposable plastic valve 110 which can withstand a conventional sterilization process.

The apparatus of the present invention individually connects a fluid solution through an input site 18 in the valve 110 with an output passageway 114 through the rotary core member 112 of the valve 110. The output passageway 114 is directly connected with the catheter tube 20. During the time interval in which the rotary core member 112 is turned to switch the connection from one solution to another, there is an instant in which both the input site 18 and the conduit 50 are exposed to the output passageway 114. Then there is an interval in which solely the neutral solution is pumped from conduit 50 through the catheter tube 20. Thus, the flow of fluid into the catheter tube 20 is continuous and is never interrupted. As the rotary core member 112 is turned to switch from conduit 50 to an input site 18, the flow of fluid into the catheter tube 20 is similarly continuous and never interrupted.

Figure 7:
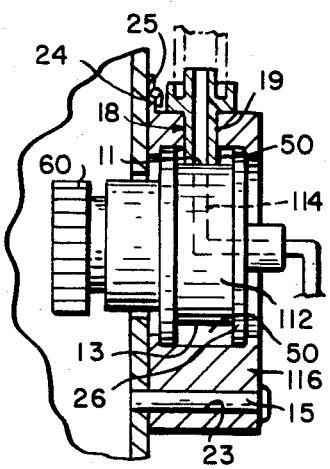
FIG. 7 is a sectional view taken along lines 3—3 of the valve in FIG. 6.

Referring now to FIGS. 6 and 7, the valve of the present invention may be described in greater detail. The valve 110 is supported in a hollow cylindrical housing 116. The housing 116 is mountable on the apparatus 120 by its mounting holes 15 and a lip 24. At the top of the valve 110, lip 24 extends outward so as to fit under ridge 25 which extends from control apparatus 120. Pins 23 projecting out of the control apparatus 120 snap into the mounting holes 15. Any conventional mounting means may be substituted for the mounting holes 15 and lip 24 as long as the valve 110 can be securely held in place and may be easily dismounted for replacement with a new sterile valve 110.

The housing 116 includes a plurality of input sites. In the preferred embodiment, there is one primary site 17 and a plurality of secondary sites 18. Each input site is a hole through the circumference of the hollow housing 116. The input site accommodates a hollow cylindrical shaft. In the case of the secondary input sites, the hollow cylindrical shafts 19 extend through the hollow housing 116 and into contact with sealing means surrounding the rotary core member 112. In the preferred embodiment, it is the circumference 13 of the rotary core member 112 which contacts and seals the cylindrical shafts 19. The ends of the shafts 19 are ground with a curve matching that of the circumference 13 of the rotary core member 112 so that the shafts lie flush against the circumference 13 to effectuate a seal. It would be possible however to provide a washer type device about the rotary core member to function as the sealing means.

The output passageway 114 extends through rotary core member 112 from an access hole 11 in the circumference 13. When the access hole is not aligned with a secondary input site 18, that input site 18 will be sealed closed by the circumference 13. The primary input site 117 has a shaft 21 which does not extend to the sealing means on the rotary core member 112. Thus, access is always maintained between the primary input site 17 and a conduit 50 which surrounds the rotary core member 112. In the presently preferred embodiment, the conduit 50 is formed by the rotary core member 112 itself. The rotary core member 112 is spool-shaped to form the channel-like conduit 50 about its circumference. The conduit 50 is formed with circumference 13 as the floor and sidewalls extending from the planar surface ends of the core member 112. The conduit 50 is wider than the outer circumference of the hollow cylindrical shafts 19. Thus, as shown in FIG. 7, the conduit 50 extends around each of the secondary input sites. This enables the neutral solution which is fed through the primary input site 17 to fill the conduit 50 all the way around the rotary core member 112.

The conduit 50 simplifies the sequential switching operation of valve 110. Since treatments involve a plurality of drugs, it is desirable to avoid substantial mixing of the drugs in the catheter tube 20. To accomplish this, the neutral solution is accessed after each use of a drug solution. The conduit 50 provides access to the neutral solution between adjacent secondary input sites 18. Thus, the core member 112 can rotate directly from one solution to another and still access neutral solution in between. This construction also promotes protection against air bubbles in the line. The access hole 11 is made wider than the walls of the hollow shafts 19 so that fluid can be continuously pulled through the catheter tube 20. As the access hole 11 is moved out of direct alignment with a secondary input site 18, it will be instantaneously exposed to solution from the input site 18 and from the conduit 50. Then it will allow passage solely of the neutral solution from the conduit 50. Thus, there will be a continuous flow of fluid which will prevent air bubbles from ever forming within the system.

At the external end of each hollow cylindrical shaft 19, there is a male luer connector for mating with a female luer connector on the polymer catheter tube bringing fluid from the intravenous fluid solution source. Any conventional connecting means may be substituted for the present male-female luer connection.

The conduit 50 carrying the neutral solution must be sealed to prevent leakage. In the presently preferred embodiment, a double seal is provided by the rotary core member 112 against the hollow cylindrical housing 116. The outer planar surfaces of the rotary core member 112 frictionally engage an inner wall of a channel 26 within the inner circumference of the hollow cylindrical housing 116. The outermost circumference of the sidewalls of the rotary core member 112 frictionally engages the floor of the channel 26 in the hollow housing 116. The snug fit of the rotary core member within the hollow housing thus functions to seal the conduit 50.

The output passageway 114 is shown in FIGS. 6 and 7. It extends from the access hole 11 in the circumference 13 of the rotary core member 112 to an output site projecting from one of the planar surfaces of the core. A catheter tube 20 makes connection with the outer projection from the core 112 to provide a path for the fluid to follow. Automatic mechanical rotation of the valve 110 is made possible by the connection of a gear 60 to the rotary core member 112. The teeth of the gear 60 mesh with the teeth of a gear 80 within the control apparatus 120 so that a motor 70 within the control apparatus may control the operation of the valve 110. The engagement of the two gears further contributes to holding the valve 110 in its mounted position on the control apparatus 120.

Figure 8:
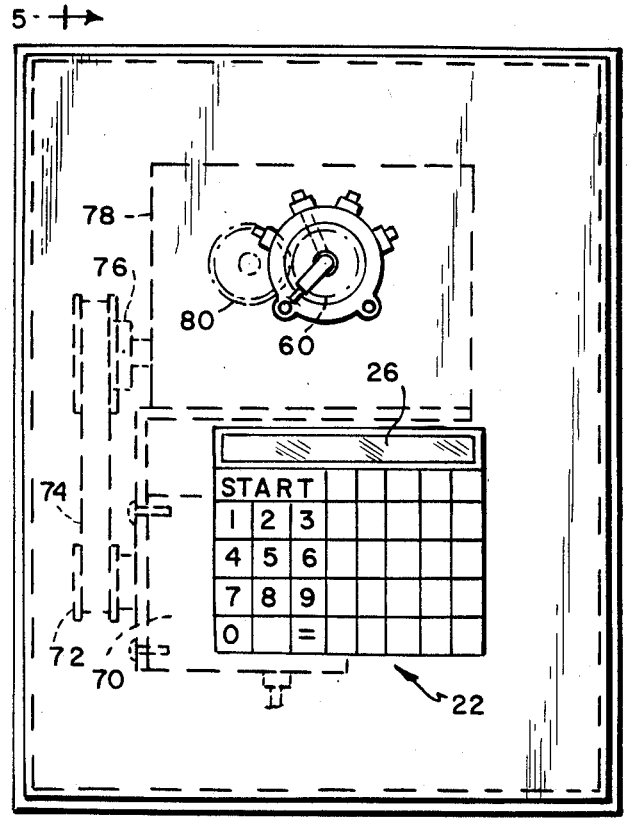
FIG. 8 is another elevational view of the apparatus of FIG. 1.
Figure 9:
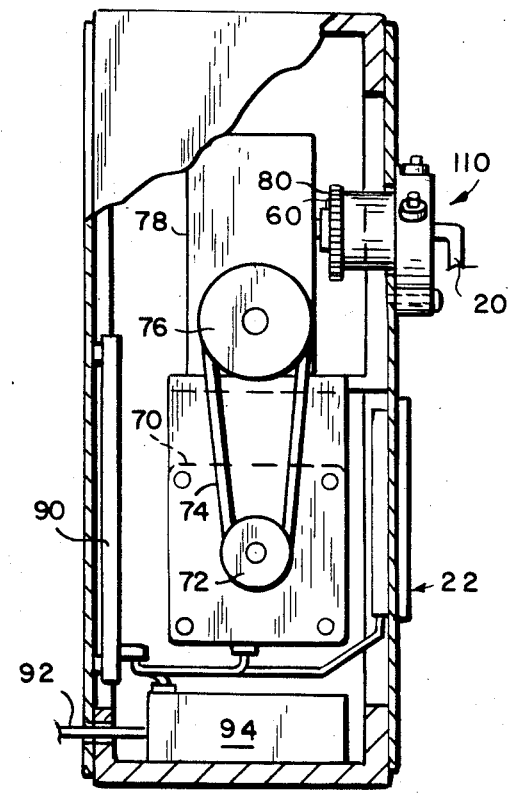
FIG. 9 is a sectional view of the apparatus of FIG. 8 taken along lines 5—5.

Referring now to FIGS. 8 and 9, the mechanics of the control apparatus 120 may be explained. A stepping motor 70 rotates a pulley 72. The pulley 72 is connected by a belt 74 to a pulley 76 on a speed reducer 78. The belt 74 thus drives the speed reducer 78. The speed reducer 78 transmits torque from the motor 70 to a gear 80 which is enmeshed with the gear 60 on the valve 110. In the presently preferred embodiment, the speed reducer uses a ratio of 48 to 1. In reducing the speed, the speed reducer 78 effectively increases the torque which is applied to the gear 60 on the valve 110. The increased torque enables the rotary core member 112 to turn against the friction from the hollow housing. Any conventional means of speed reduction may be substituted for the present drive train.

The stepping motor 70 is controlled by a microprocessor located on a circuit board 90 at the rear of the control apparatus 120. Power for the microprocessor circuitry and the motor 70 is provided from a line cord 92 which is connected through a power supply 94. It is preferable to include a backup battery supply which would be automatically switched on should the power supplied over the line cord 92 be disrupted. The microprocessor circuitry also receives inputs from the control panel 22. The control panel 22 is used to program the microprocessor so that one control apparatus 120 may be used to operate the valve 110 for administering an unlimited variety of prescribed regimens.

The apparatus of the invention makes possible the administration of advanced treatments using a plurality of drug solutions. The use of a greater variety of drug solutions is possible since the apparatus allows the use of a neutral solution as a spacer to prevent substantial mixing of the drug solutions in the catheter tube 20. The operation of the apparatus begins with mounting the valve 110 on the control apparatus 120. The fluid solutions are connected to the input sites 18 of the valve 110. A pump 140 is coupled to the catheter tube 20. The pump 140 is turned on and the catheter set is purged of air. The operator causes the valve 110 to turn through each input site position by pressing an appropriate button on the control panel 22. The controls and microprocessor means for implementing the controls may be provided by one skilled in the art. The operator leaves the valve 110 in each input site position until all air bubbles have been removed. The pump is then turned off.

The apparatus may now be initialized. The microprocessor memory is cleared. The volume of the neutral solution source is entered. The volume of the spacer size which is prescribed for use between the fluid solutions is entered. Then the volume of the other fluid solution sources and their prescribed rates of infusion are entered. The pumping rate or speed of pump 140 and the total volume of fluid to be infused per unit time are computed automatically and displayed to the operator on a display 26. The operator then instructs pump 140 to infuse at this speed and for this total volume. After the information has been fed into the microprocessor, thereby programming the apparatus to administer the prescribed regimen, the intravascular access needle on the catheter tube 20 is inserted into the patient and the pump 140 and control apparatus 120 are started.

The infusion process then proceeds automatically. The control apparatus 120 may be provided with an alarm that would sound after a calculated time period elapses which indicates that a solution is in need of refilling. A nurse would stop the pump and press a pause button on the control panel 22. The fluid source would be replaced or refilled. The line is purged if necessary. The new volume of fluid is entered into the control panel 22. Any necessary changes may be made to other variables entered into the apparatus. Then the pump 140 and control apparatus 120 may be restarted.

The apparatus of the present invention only requires a single pump and catheter tube to deliver all of the fluid solutions to the patient. The control panel can be programmed to set the amounts of fluid solutions to be provided to the patient, thereby satisfying a physician's particularly prescribed regimen. The valve of the invention is designed to effectively seal each of the drug solutions from one another so that no undesirable precipitates or reactions occur prior to the infusion. This invention thereby advantageously expands the number of drug solutions available to physicians for use in multiple drug infusion treatments. The neutral solution may be easily accessed between the input sites of the other fluid solutions to provide a spacer between the solutions in the catheter tube 20.

The valve assembly is made of a plastic that may be sterilized by a conventional method. It may be easily mounted and dismounted from the control apparatus so that it may be replaced by a new, sterile valve as needed. The disposability of the valve enhances the integrity of the sterility of the infusion system. The apparatus of the present invention has thus made possible a new and simplified method for administering a number of drug solutions to a patient through a single catheter tube attached to a single pump, without substantially mixing the drugs in the catheter tube.

According to the method of the present invention, the spacer solution 10 is provided for substantially isolating the different fluid solutions during intravenous administration. FIG. 2 shows a first solution 12 and a second solution 14 separated by the spacer solution 10. The solutions are carried by a catheter tube 20 through a needle and into a patient. Pump 140 keeps the fluids moving through the catheter tube 20 at a predetermined rate. The spacer solution 10 must be a solution which is suitable for intravenous infusion into a patient. The spacer 10 must also be neutral with respect to each of the fluid solutions on either side of it. In other words, the spacer solution 10 must not substantially react with either the first fluid solution 12 or the second fluid solution 14 while it is traveling through the catheter tube 20 into the patient. Some solutions may react with one another over a long period of time, however, it is only necessary that there be no adverse reactions prior to the infusion.

There are a number of intravenous solutions which may be selected as the neutral spacer 10, including but not limited to saline solutions, dextrose solutions and intravenous lipid solutions. The appropriate spacer solution 10 should be selected according to a patient's needs. For example, a patient requiring nutritional supplement may receive a high concentration dextrose solution as the spacer, whereas a patient merely requiring liquids may receive a saline solution or a low concentration dextrose solution.

The volume of the spacer solution 10 affects the rate of mixing between the fluid solutions on adjoining sides of the spacer. A spacer with a low volume would have a tendency to allow the adjoining fluids to diffuse more quickly into each other. On the other hand, a spacer with a larger volume would decelerate the rate of diffusion of adjoining drug solutions into each other.

The volume of the spacer solution must be selected so as to avoid substantial mixing between the fluid solutions on either side of the spacer solution 10 in the time that the solutions are in transit within the catheter tube 20. If the diffusion rate between a fluid solution and the spacer solution 10 is rapid, the spacer solution 10 must have a greater volume to avoid mixing of the two isolated fluid solutions. Some insubstantial mixing may be allowed where the first drug solution 12 and the second drug solution 14 are relatively compatible with one another and will not react when in contact to a small extent. For more highly reactive fluid solutions, any amount of mixing would be substantial and must be prevented. Thus, the appropriate volume of spacer 10 depends on a variety of factors.

Because of laminar flow which occurs during the movement of fluids through the catheter tube 20, the type of pump being used will also be determinative of the minimum volume of spacer solution 10 required to separate the first and second fluid solutions. Referring now to FIG. 3, the affects of laminar flow of fluids as they travel through the catheter tube 20 is shown. There is friction between the walls of the catheter tube 20 and the fluids which are flowing through it. This friction slows the outer layers of fluid. Thus, the fastest flowing fluid is found along the center axis of the catheter tube 20. Over a period of travel through the tube the spacer solution 10 develops a convex pointed front side and a concave indented rear side. The volume of spacer solution 10 must be prescribed to be large enough so that the rear edge of the first fluid solution 12 does not substantially overlap the leading front point of fluid solution 14. A cross-section showing such an overlap is illustrated in FIG. 3 at cross-section 16. A peristaltic pump 30, illustrated in FIG. 4, operates by squeezing the catheter tube 20. If there is a cross-section 16 including the first and second fluid solutions as they reach the peristaltic pump 30, upon being squeezed by pump 30 the two solutions would be in direct contact as a result of the pump action. Therefore, it is important that when using a peristaltic pump 30 that there be a cross-section 17 maximally filled with spacer solution 10 as the spacer solution reaches the peristaltic pump 30.

A syringe-type cartridge pump 40, also known as volumetric pump, illustrated in FIG. 5 works in a different manner. The cartridge pump 40 operates by filling and emptying a chamber 42. A valve 44 rotates to switch between a filling and an emptying position. To prevent substantial mixing between fluid solution 12 and second fluid solution 14, it is again necessary to prescribe a sufficient volume of spacer solution 10 to substantially isolate the two fluid solutions. To accomplish this, the spacer solution 10 should encompass a volume which fills a cylindrical cross-section 19 of the tube which is equal to or greater than the volume of the chamber 42. Thus, the pump chamber 42 will be prevented from substantially filling with more than one of the fluid solutions separated by the spacer 10.

The treatment variations made possible by the method of the present invention are numerous. Various drugs, nutrients, electrolytes or other items capable of being delivered in fluid solutions may be sequentially infused into a patient according to the present invention. The number of fluid solutions which may be sequentially infused into a patient are only limited by the ability to connect the solutions by valves to a catheter tube in a manner which continuously administers fluids without allowing any air bubbles into the line. The compatibility and stability of the various fluid solutions with one another are now of less importance. Almost any drug solution which can produce synergistic effects when used in combination, may be infused according to the method of the present invention. By frequently alternating between fluid solutions and spacer, several drug solutions can be administered to a patient in sequence over and over again without the problem of substantial mixing prior to infusion. The patient is thus able to obtain many benefits which may derive from the combination of a plurality of drug solutions. Many new drug solution combinations will be made possible through the use of the present invention.

Of course, it should be understood that various changes and modifications to the preferred embodiments described above will be apparent to those skilled in the art. Any intravenous solution which does not react with adjoining fluid solutions may be substituted for the saline, dextrose and lipid solutions of the present invention. These and other changes can be made without departing from the spirit and the scope of the invention and without diminishing its attendant advantages. It is therefore intended that such changes and modifications be covered by the following claims.

We claim:

1. A method for sequential intravenous administration of a plurality of fluid solutions, said method comprising:
    providing a valve that provides continuous communication between an output and at least one of a plurality of inputs;
    connecting a neutral solution to one input of said valve;
    connecting each of said plurality of solutions to different inputs of said valve;
    connecting a lumen of a catheter tube to the output of said valve; and
    using an electronic processor to alternately switch said valve between the input connected to said neutral solution and one of said other plurality of inputs at predetermined intervals, said neutral solution being provided between said fluid solutions to prevent said fluid solutions from substantially mixing in said lumen of said catheter tube.

* * * * *